United States Patent
Bevinakatti et al.

(10) Patent No.: US 12,290,590 B2
(45) Date of Patent: May 6, 2025

(54) BIODEGRADABLE POLYESTERS FOR WATER-RESISTANT ANHYDROUS SUNCARE FORMULATIONS

(71) Applicant: NOURYON CHEMICALS INTERNATIONAL B.V., Amhem (NL)

(72) Inventors: Hanamanthsa Shankarsa Bevinakatti, Somerset, NJ (US); Paul Michael Ferm, Morristown, NJ (US); Allison M. Johnston, Whippany, NJ (US); William F. Joyce, Hopewell, NY (US); Karen L. White, Bridgewater, NJ (US); Kristin Nicole Golas, Raritan, NJ (US)

(73) Assignee: NOURYON CHEMICALS INTERNATIONAL B.V., Amhem (NL)

( * ) Notice: Subject to any disclaimer, the term of this patent is extended or adjusted under 35 U.S.C. 154(b) by 428 days.

(21) Appl. No.: 17/176,484

(22) Filed: Feb. 16, 2021

(65) Prior Publication Data
US 2021/0259946 A1  Aug. 26, 2021

Related U.S. Application Data

(60) Provisional application No. 62/979,705, filed on Feb. 21, 2020.

(51) Int. Cl.
| | | |
|---|---|---|
| *A61K 8/85* | (2006.01) | |
| *A61Q 17/04* | (2006.01) | |
| *C08G 63/199* | (2006.01) | |
| *C08G 63/21* | (2006.01) | |

(52) U.S. Cl.
CPC ............. *A61K 8/85* (2013.01); *A61Q 17/04* (2013.01); *C08G 63/199* (2013.01); *C08G 63/21* (2013.01); *A61K 2800/31* (2013.01); *A61K 2800/54* (2013.01); *A61K 2800/74* (2013.01)

(58) Field of Classification Search
None
See application file for complete search history.

(56) References Cited

U.S. PATENT DOCUMENTS

| | | |
|---|---|---|
| 5,885,596 A | 3/1999 | Parab |
| 6,242,499 B1 | 6/2001 | Gruning et al. |
| 6,409,997 B1 | 6/2002 | Castro |
| 8,465,730 B1 | 6/2013 | O'Lenick |
| 10,039,700 B2 | 8/2018 | He et al. |
| 2002/0197292 A1 | 12/2002 | Fowler |
| 2003/0232962 A1 | 12/2003 | Scholl et al. |
| 2004/0005278 A1 | 1/2004 | Reinhart et al. |
| 2006/0008426 A1 | 1/2006 | Doring et al. |
| 2006/0151109 A1 | 7/2006 | Carter et al. |
| 2008/0188569 A1 | 8/2008 | Takeda et al. |
| 2010/0047194 A1 | 2/2010 | Bevinakatti et al. |
| 2011/0091397 A1 | 4/2011 | Zhang et al. |
| 2014/0242014 A1 | 8/2014 | Yoriko et al. |
| 2017/0002134 A1 | 1/2017 | Smits et al. |
| 2018/0318193 A1 | 11/2018 | He et al. |
| 2018/0320096 A1 | 11/2018 | Craige et al. |
| 2019/0202771 A1 | 7/2019 | Von Hof et al. |
| 2020/0093716 A1* | 3/2020 | Swoboda .............. A61K 8/31 |
| 2021/0346264 A1 | 11/2021 | Denda et al. |
| 2021/0369911 A1* | 12/2021 | Stumbé .............. C08G 18/73 |

FOREIGN PATENT DOCUMENTS

| | | | |
|---|---|---|---|
| EP | 1549281 B1 | 1/2007 | |
| EP | 1857091 A1 | 11/2007 | |
| EP | 2 359 803 A1 | 8/2011 | |
| EP | 2359803 B1 | 6/2014 | |
| JP | 2005 132729 A | 5/2005 | |
| JP | 2005179377 A | 7/2005 | |
| JP | 2007284371 A | 11/2007 | |
| JP | 2010143834 A | 7/2010 | |
| WO | WO-2020116439 A1 * | 6/2020 | ............. A61K 8/361 |

OTHER PUBLICATIONS

Color Cosmetic Ingredients, Happi Household and Personal Products Industry, Rodman Publishing, Ramsey, NJ, US, vol. 41, No. 8, Aug. 1, 2004, pp. 71-76.

* cited by examiner

*Primary Examiner* — Nannette Holloman
(74) *Attorney, Agent, or Firm* — LKGLOBAL | Lorenz & Kopf, LLP

(57) ABSTRACT

The present disclosure generally relates to a waterproofing polymer that is a substantially non-sequential reaction product of the following components: (i) at least one polyglycerol; (ii) at least one dimer acid; and (iii) at least one fatty acid having 8-30 carbon atoms, wherein (iii) and (i) are in a molar ratio of less than 2:1. The components are charged to a reaction vessel and subsequently reacted to produce a polyester polymer having excellent waterproofing properties. The polymers impart high static and water-resistant SPF to anhydrous sunscreen formulations.

38 Claims, 1 Drawing Sheet

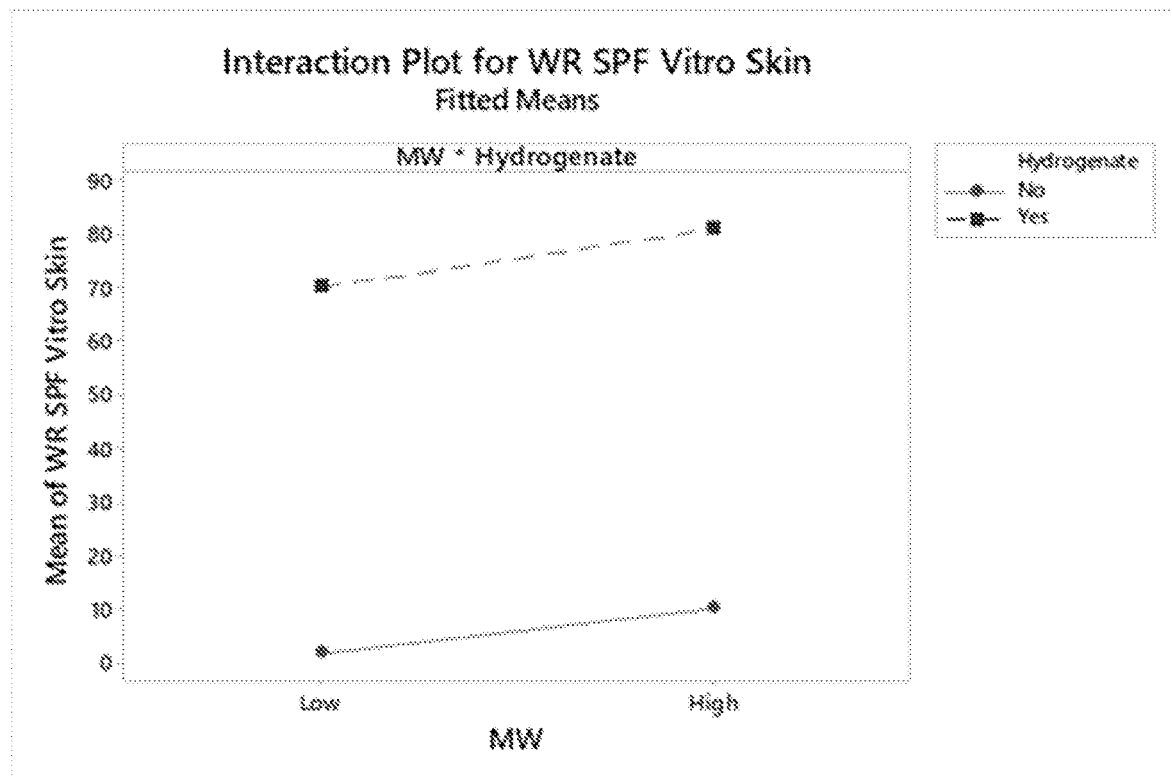

BIODEGRADABLE POLYESTERS FOR WATER-RESISTANT ANHYDROUS SUNCARE FORMULATIONS

PRIORITY CLAIM

This application claims benefit of U.S. Provisional Application Ser. No. 62/979,705, filed Feb. 21, 2020, the entire contents of which are hereby incorporated herein by reference.

FIELD OF THE DISCLOSURE

The present disclosure generally relates to new biodegradable polyesters, processes for preparing them, and their use in water-resistant anhydrous suncare formulations.

BACKGROUND OF THE DISCLOSURE

Sunscreen formulations have become important for consumer uses in which heavy sun exposure is to be managed without experiencing severe erythemia (sunburn) during extensive periods of sun exposure with or without periods of exercise, which, in turn, can take place either with or without water immersion. Sunscreens are stringently controlled and measured using standardized sun protection factor (SPF) tests. Each product introduced to the market must be labeled with the lesser of two SPF measurements. The Static SPF measurement, designated "SPF," is taken immediately after a specified amount of sunscreen formulation is applied to the skin, dried for a fixed period of time, typically 15 to 30 minutes, and then tested for SPF without further activity. The Water-resistant SPF measurement, or "WR SPF," is taken from the same test subject, after immersion in water for specified period of time, a "Highly Water-resistant" SPF, is taken after 80 minute submersion in water held at 40° C. and is the measurement of focus hereafter referred to as "WR SPF". Sunscreen formulations contain so-called active materials that either absorb or scatter UV light of specified wavelengths. These actives, however, do not exhibit the film-formation or water-resistant properties needed to provide the applied sunscreen formulation with WR SPF values of current interest, especially in the range of WR SPF 30, 50, 70, 90, or 100. Instead, a class of materials, typically polymers, are used to provide film-former and water-resistant properties and are the subject of this disclosure.

Sunscreen film-formers for water resistance have been known for a long time. Synthetic polymers, including PVP/olefin copolymers and acrylate copolymers, have been developed that give water resistance depending on their dose (both SPF and WR SPF from SPF 15 to SPF 50 and above). These materials can have molecular weights of around 50,000 Daltons to more than 1,000,000 Daltons (Da). These synthetic polymers provide high SPF and WR SPF of 50 or more with polymers loadings in the emulsion of around 2 wt %, but they are also non-biodegradable and therefore undesirable for the environment. Currently, scrutiny is being placed on all such "microplastics," which are released to the water during uses, such as swimming and snorkeling, and do not compose in the environment.

More biodegradable hydrophilic and hydrophobic polyesters have been developed as additives to cosmetics and some have been recommended for sunscreens. However, they only seem appropriate for LOW WR SPF formulations (i.e. those with relatively low levels of water resistance and WR SPF ratings of 15 or perhaps 30.) When tested in a standard SPF50 formulation used in this specification, these materials do not provide any appreciable WR SPF (SPF ~2 being measured for a 2 wt % polymer loading).

Accordingly, high SPF and WR SPF sport sunscreen manufacturers remain under market and regulatory pressure to provide more natural products with zero microplastic content. Ganex™ polymers [e.g., Antaron™ V-220F Polymer (INCI: VP/Acrylates/Lauryl Methacrylate Copolymer)] are currently very commonly used and are able to endow sunscreen formulations with high SPF values of 50 or more, while also providing WR SPF values of 50 or more, i.e. water and wear resistance, but, again, these polymers are not biogradable.

Gruning et al., U.S. Pat. No. 6,242,499, describe polyesters obtained by esterification of a polyglycerol mixture with saturated or unsaturated, linear or branched fatty acids having 12 to 22 carbon atoms and polyfunctional carboxylic acids having 4 to 54 carbon atoms and a mean functionality of from 2 to 2.4, the degree of esterification of the polyglycerol mixture being between 30 and 75%. The only described preparation procedure involves esterifying polyglycerol with fatty acid in a first step and, after most, or all, of the fatty acid has reacted, in a second step adding polyfunctional carboxylic acid and continuing the esterification reaction. The polyesters obtained are described as being useful as water-in-oil emulsifiers in the preparation of cosmetic or pharmaceutical preparations, including sun-protection creams, but there is no teaching or suggestion that the polyesters are useful as sunscreen film-formers for water resistance. Indeed, the polyesters obtained, while being biodegradable, are characterized by low WR SPF values.

O'Lenick, U.S. Pat. No. 8,465,730, describes sunscreen formulations characterized by a synergistic effect between sunscreening actives and a waterproofing polyester prepared by reacting a mixture of polyglycerol, a diacid, and a mixture of at least two different fatty acids. The data supporting the improvement are very limited. In one case, a polyester prepared by reacting polyglyceryl, stearic acid, isostearic acid, and a hydrogenated C34 dimer acid (Example 35) provided a static SPF of 42. In the other case, a polyester prepared by reacting polyglyceryl, oleic acid, stearic acid, and azelaic acid (Example 68) provided a static SPF of 39. While these values were somewhat higher than values given using polymers prepared according to a prior art patent, they are only focused on the static SPF and were not tested by standard water-immersion protocols that are required to be classified by the FDA and other agencies as water-resistant or very water resistant WR SPF. These polymers do not provide the values expected by those skilled in the art for water-resistance in suncare formulations as provided by the synthetic Ganex™ polymers.

Non-aqueous, i.e., anhydrous, sunscreen formulations are those that are typically solvent based compositions that can be formed as gels for topical application or sprayed on, for example from an alcohol-based solution of the ingredients.

Sprayable sunscreen compositions have become popular in recent years as a means for transporting and applying sunscreen. Film-forming polymers are known to be added to non-aqueous sunscreen compositions to provide water resistance to these compositions after application to a surface such as skin or hair. The best-performing film-forming polymers used in such formulations are also biodegradable.

Thus, there remains an unfulfilled need in the art to provide a bio-based, biodegradable polymer with excellent sensory, waterproofing, and Water-resistant Sun Protection Factor (WR SPF) performance in addition to the requisite static SPF (SPF) performance, wherein the polymer is natural and biodegradable and performs strongly in anhydrous sport sunscreens to resist water from diluting and removing UV absorbers after application. These and other objectives are met by the present disclosure.

SUMMARY OF THE DISCLOSURE

U.S. Provisional Application Ser. No. 62/979,566 (hereinafter "the copending application"), filed Feb. 21, 2020, describes a waterproofing polymer that is a substantially non-sequential reaction product of the following components: (i) at least one polyglycerol; (ii) at least one dimer acid; and (iii) at least one fatty acid having 8-30 carbon atoms, wherein (iii) and (i) are in a molar ratio of less than 2:1. All details concerning the preparation of that waterproofing polymer, including all individual embodiments described in the copending application relating to such preparation and all limitations regarding the structure and properties of the waterproofing polymer itself are hereby incorporated herein by reference. We have found that the waterproofing polymer, which is described in the copending application as being useful to impart high static and water-resistant SPF to oil-in-water sunscreen formulations is also useful to impart high static and water-resistant SPF to anhydrous sunscreen formulations.

The present disclosure generally relates in another embodiment to an anhydrous formulation comprising the disclosed waterproofing polymer.

The present disclosure generally relates in another embodiment to an anhydrous sunscreen formulation comprising the following distinct ingredients: (a) at least one sunscreen active agent; and (b) at least one waterproofing polymer as disclosed herein.

By "distinct ingredient" is meant that one ingredient does not satisfy more than one of the recited ingredients. For example, consider a composition comprising distinct ingredients (a), (b), and (c). In such example, there must be a minimum of three ingredients combined to satisfy (a), (b), and (c), with a first ingredient satisfying (a), a second different from said first ingredient satisfying (b), and a third different from said first and second ingredients satisfying (c).

The present disclosure generally relates in yet another embodiment to a method of protecting a user to be exposed or already exposed to sunlight from the damaging effects of exposure to sunlight comprising applying to skin of said user an effective amount therefor of an anhydrous sunscreen formulation as disclosed herein.

The present disclosure generally relates in a still further embodiment to a method for waterproofing an anhydrous sunscreen formulation comprising at least one sunscreen active agent, said method comprising incorporating in said sunscreen formulation a waterproofing amount of at least one waterproofing polymer as disclosed herein.

BRIEF DESCRIPTION OF THE DRAWING

The disclosure will now be described in greater detail with reference to the drawing, wherein:

The FIGURE is a graph illustrating the benefits of using hydrogenated dimer acid to prepare a waterproofing polymer according to the present disclosure using the disclosed substantially non-sequential reaction method and the effect of weight-average molecular weight of the polymer on WR SPF.

DETAILED DESCRIPTION OF THE PREFERRED EMBODIMENTS

The present disclosure generally relates to a waterproofing polymer capable of imparting high static and water-resistant SPF to anhydrous sunscreen formulations.

A key stated benefit of this invention is to provide a bio-based, biodegradable polymer with excellent sensory, waterproofing, and excellent Water-Resistant Sun Protection Factor (WR SPF) performance that is natural and biodegradable and performs strongly in anhydrous sport sunscreens to resist water from diluting and removing UV absorbers after application. An acceptable high WR SPF goal is considered to be SPF 50.

The disclosed waterproofing polymer is the substantially non-sequential reaction product of the following components: (i) at least one polyglycerol; (ii) at least one dimer acid; and (iii) at least one fatty acid having 8-30 carbon atoms.

By "substantially non-sequential reaction product" is meant the product is produced by substantially non-sequential reaction of the reacting components (i)-(iii). By substantially non-sequential reaction of the reacting components (i)-(iii) is meant substantially the total content of each of the reactants (i)-(iii) to be reacted is added to the reaction vessel prior to commencing the reaction. This processing is distinct, for example, from that described in U.S. Pat. No. 6,242,499, wherein polyglycerol is esterified with fatty acid in a first step and, after most, or all, of the fatty acid has reacted, in a second step polyfunctional carboxylic acid is added and the esterification reaction is continued. In one embodiment of the present disclosure, the total content of each of the reactants (i)-(iii) to be reacted is added to the reaction vessel prior to commencing the reaction, i.e., the reaction is completely non-sequential, and the polymer is a completely non-sequential reaction product of the components (i)-(iii). In other embodiments, at least 70-100%, or 75-100%, or 80-100%, or 85-100%, or 90-100%, or 95-100%, or 97-100% of each of the reactants (i)-(iii) is added to the reaction vessel prior to commencing the reaction.

While not wishing to be bound by theory, we believe that the preparation procedure described in U.S. Pat. No. 6,242,499, involving reaction of polyglycerol with monofunctional fatty acid in a first step, leads to undesirable premature chain-termination or "end-capping." Reaction with monofunctional fatty acid not only reduces the number of free hydroxyl sites available for reacting with polyfunctional carboxylic acid in the second step, but the fatty acid ester functional groups produced in the first step are substantially inert and, thus, not available to participate in chain-extension or branching. This has significant effects on the properties of the polymers thus produced. Introducing substantially all or the total content of the components (i)-(iii) to the reaction vessel at the outset and/or prior to commencing the polymer reaction, as described herein, ensures minimal inhibition by the fatty acid on the ability of the polyfunctional carboxylic acid(s) to react with the polyglycerol, leading to longer polymer chains and more extensive polymer chain crosslinking, higher polymer molecular weights, and higher viscosities.

The polyglycerol can be any oligocondensation product of glycerol. In one embodiment, the polyglycerol has the formula (I):

$$H[-O\text{-Gly-}]_n\text{-OH} \qquad (I)$$

where each Gly is independently the residue of a molecule of glycerol after removal of two hydroxyl groups; and n is (an average of) from 2 to 10.

Generally, most of the groups Gly will be of the formula: $-CH_2-CHOH-CH_2-$, although residues comprising etherification at the secondary or even tertiary hydroxyl groups are considered to be within the scope of "Gly" and, thus, may also be present. Examples of oligoglycerols include diglycerol, triglycerol, tetraglycerol, pentaglycerol, hexaglycerol, heptaglycerol, nonaglycerol, decaglycerol, and mixtures of these. Particularly useful polyglycerols are those of the formula (I) where n is particularly from 2 to 7, more particularly from 2 to 5 and especially 2, 3 or 4, or mixtures of oligoglycerols in these ranges.

Particularly suitable polyglycerols comprise a mixture of oligoglycerols having the following oligomer distribution:
 Glycerol: 0 to 30% by weight, preferably 0 to 20% by weight, most preferably 0 to 15% by weight
 Diglycerol: 10 to 40% by weight, preferably 15 to 35% by weight, most preferably 20 to 32% by weight
 Triglycerol: 10 to 65% by weight, preferably 15 to 60% by weight, most preferably 18 to 55% by weight
 Tetraglycerol: 2 to 25% by weight, preferably 5 to 20% by weight, most preferably 8 to 20% by weight
 Pentaglycerol: 0 to 15% by weight, preferably 0 to 10% by weight, most preferably 0 to 5% by weight
 Hexaglycerol: 0 to 15% by weight, preferably 0 to 10% by weight, most preferably 0 to 5% by weight
 Heptaglycerol: 0 to 10% by weight, preferably 0 to 5% by weight, most preferably 0 to 3% by weight
 Octaglycerol: 0 to 10% by weight, preferably 0 to 5% by weight, most preferably 0 to 3% by weight
 Nonaglycerol: 0 to 5% by weight, preferably 0 to 3% by weight, most preferably 0 to 2% by weight
 Decaglycerol: 0 to 5% by weight, preferably 0 to 3% by weight, most preferably 0 to 2% by weight
wherein all weight percentages are based on a total content of the polyglycerol.

In one embodiment, the polyglycerol comprises the following oligomer distribution:
 Glycerol: 0 to 30% by weight
 Diglycerol: 15 to 40% by weight
 Triglycerol: 10 to 55% by weight
 Tetraglycerol: 2 to 25% by weight
 Pentaglycerol and higher components: 0 to 15% by weight
wherein all weight percentages are based on a total content of the polyglycerol.

In one embodiment, the polyglycerol is composed of at least 40% by weight, or at least 45% by weight, or at least 50% by weight, based on a total weight of the polyglycerol, of a combination of diglycerol and triglycerol.

In one embodiment, the polyglycerol is composed of at least 20% by weight, or at least 25% by weight of diglycerol; at least 15% by weight, or at least 18% by weight of triglycerol; at least 10% by weight, or at least 12% by weight of tetraglycerol; wherein all weight percentages are based on a total content of the polyglycerol.

A particularly preferred polyglycerol comprises at least 25% by weight diglycerol, at least 45% by weight triglycerol, and at least 10% by weight tetraglycerol.

Analysis of any such polyglycerol composition can be done to determine it's median, mean, or "average" polyglycerol number. Oligoglycerol examples above with both narrow and broad distributions can be equally designated as polyglycerol-3, as this is the closest integer to the mean and/or median.

The dimer acid can be any dicarboxylic acid having at least 4 carbon atoms. They can be straight-chain or branched, such as, for example, dimers prepared from malonic acid, succinic acid, fumaric acid, dimethylglutaric acid or trimethyladipic acid, and their anhydrides.

Dimer fatty acids are especially useful. As is known, these are mixtures of acyclic and cyclic dicarboxylic acids which are obtained by a catalyzed dimerization reaction of unsaturated fatty acids having 12 to 22 carbon atoms.

For the preparation and use of dimer acids and their physical and chemical properties, reference is made to the publication "The Dimer Acids: The chemical and physical properties, reactions and applications", Ed. E. C. Leonard; Humko Sheffield Chemical, 1975, Memphis, Tenn.

The dicarboxylic acids can also contain, to a lesser extent, tri- and polyfunctional carboxylic acids. The functionality of the mixture should not exceed a value of 2.4 molar average.

We have found that the use of higher molecular weight dimer acids provides a beneficial combination of significant hydrophobic character to enhance waterproofing. Preferred are those dimer acids typically derived from triglycerides rich in C18 ester groups, which can be hydrolyzed to produce C18 unsaturated monoacidic fatty acids. The raw materials can be derived from tall oil and rapeseed oil, but other natural sources including flaxseed, soybean, pumpkin, walnut can be used. The target monoacids used in the reaction are rich in oleic and linoleic acid forms described in the fatty acid listing contained below. Dimerization leads primarily to the dimerization of unsaturated fatty acids, however trimers are also formed. After reaction, the product can be kept as a mixture of reaction products or it can be further distilled or otherwise separated into molecular weight fractions. In one embodiment, the dimerization reaction produces a majority (at least 60 wt %, more preferably at least 75 wt %) of dimer acid (C36 diacid) but also produces C54 trimer acids (less than 30 wt %, more preferably less than 25%) and contains residual C18 acid and C27 1½-mers.

In one case, commercially available standard dimer acid from Croda, Pripol 1025, is used which contains 7 wt % total of C18 monomer and C27 1½-mer, 72 wt % dimer, and 19 wt % trimer acid. In another case, hydrogenated standard dimer acid from Oleon, Radiacid 0960, is used which contains 3 wt % C18 monomer and C27 1½-mer, 87 wt % dimer, and 10 wt % trimer acid. In both cases, the polymer as described is characterized by higher molecular weight, more hydrophobic character, and higher viscosity than can be provided by pure, lower molecular weight, diacids. The presence of trimer acid further enhances the molecular weight and performance of these polymers.

Hydrogenation of the dimer acid is a critical factor affecting important properties of the polymers. In particular, the use of hydrogenated dimer acid to prepare the disclosed polymers dramatically increases water-resistance and SPF performance of the resulting suncare and cosmetic formulations.

Thus, in one embodiment, the present disclosure relates to a waterproofing polymer prepared from at least one hydrogenated dimer acid.

In another embodiment, the waterproofing polymer is prepared from a hydrogenated dimer acid comprising hydrogenated dimerized C18 fatty acids, which hydrogenated dimer acid is obtained through dimerization of unsaturated C18 fatty acids and subsequent hydrogenation.

It is beneficial if the hydrogenated dimer acid contains a content of trimer acid as this increases branching and polymer molecular weight.

In one embodiment, the hydrogenated dimer acid contains a trimer acid content ranging from about 5-25 wt %, based on a total weight of hydrogenated dimer acid.

In another embodiment, the hydrogenated dimer acid contains a majority (at least 60 wt %, more preferably at least 75 wt %) of hydrogenated dimer acid (C36 diacid) and also contains C54 hydrogenated trimer acids (less than 30 wt %, more preferably less than 25%) and contains residual C18 hydrogenated acid and C27 hydrogenated 1½-mers.

Fatty monoacids are desired to act as end-caps of the polymerization reaction, provide tunable hydrophobic content, and contribute to polymer properties. While all monoacids having 8-30 carbon atoms can be used, especially monoacids having 12-30 carbon atoms, we prefer C18 or greater monoacids to provide greater hydrophobic content for waterproofing. These can include naturally occurring or refined fatty acids, such as hydrolyzed rapeseed oil, sunflower oils etc, however these contain both lower and higher MW chains.

Useful fatty monoacids can be linear, branched, saturated, unsaturated, and aromatic materials with acidity provided by carboxylic acid moieties. Useful acids include Caprylic acid (C8), Pelargonic acid (C9), Capric acid (C10), Undecylic acid (C11), Lauric acid (C12), Tridecylic acid (C13), Myristic acid (C14), Pentadecylic acid (C15), Palmitic acid (C16), Margaric acid (C17), Stearic acid (C18), Isostearic acid (C18), Nonadecylic acid (C19), Arachidic acid (C20), Behenic acid (C22), and Lignoceric acid (C24). (Lower molecular weight organic acids could also be used instead of the fatty monoacid including Butyric acid (C4), Valeric acid (C5), Caproic acid (C6), Enanthic acid (C7).)

Comparing stearic and isostearic acid shows that branching leads to high melting point and results in a low viscosity at room temperature for isostearic acid, vs a solid material for stearic acid. This lower viscosity can be helpful in materials handling of raw materials and also in enabling esters made with this acid to retain liquid properties. Branched-chain fatty acids often contain a single methyl branch along the linear carbon chain and are produced in nature through microbial action. Isostearic acid is available as a reaction byproduct in the creation of dimer acid described above.

Another route to obtaining a liquid product is to use unsaturated linear and branched fatty monoacids. These unsaturated acids can include Palmitoleic acid (C16:1), Vaccenic acid (C18:1), Oleic acid (C18:1), Elaidic acid (C18:1), Linoleic acid (C18:2), Linolelaidic acid (C18:2), α-Linolenic acid (C18:3), γ-Linolenic acid (C18:3), Stearidonic acid (C18:4), Paullinic acid (C20:1), Gondoic acid (C20:1), Dihomo-γ-linolenic acid (C20:3), Mead acid (C20:3), Arachidonic acid (C20:4), Eicosapentaenoic acid (C20:5), Erucic acid (C22:1), Docosatetraenoic acid (C22:4), Cervonic acid (C22:6), and Nervonic acid (C24:1). As is well-known to persons skilled in the art, the designation "CX:Y" means the length of the carbon chain is X carbon atoms; and there are Y number of double bonds in the chain.

All of these acids and mixtures thereof provide hydrophobicity when esterified with polyglycerol. Saturated fatty acids also will provide less manufacturing side reaction and greater long-term finished product storage due to oxidation of unsaturated bonds that can lead to color and other side products.

In one embodiment, the fatty acid is stearic acid, a straight-chain saturated C18 fatty acid, or oleic acid which is a mono unsaturated C18. However, points of unsaturation can provide later oxidative instability and straight linear C18 fatty acid can lead to polymer crystallization.

For this reason, we prefer isostearic acid, which provides both long-term stability and inhibits crystallization and phase separation of both the raw ingredient and final polymer.

In an especially preferred embodiment, the waterproofing polymer is a substantially or completely non-sequential reaction product of the following components: (i) at least one polyglycerol comprising at least 25% by weight diglycerol, at least 45% by weight triglycerol, and at least 10% by weight tetraglycerol, in each case based on a total weight of polyglycerol; (ii) at least one hydrogenated dimer acid containing at least 60% by weight of hydrogenated C36 diacid and 5-25% by weight of hydrogenated C54 triacid, in each case based on a total weight of hydrogenated acid; and (iii) isostearic acid.

In one embodiment, the waterproofing polymer is prepared by a one-step process that involves introducing all reactants to a reaction vessel and thereafter inducing a fully statistical addition of the dimer acid and the isostearic acid to the polyglycerol.

We have found that the best waterproofing properties of the polymer result when the polyglycerol contains excess OH groups, relative to the acid groups added by the combination of isostearic acid and dimer acid materials. As described above, a wide variety of polyglycerols have been used in blended form and deliver the unique performance given by this material.

In one embodiment, the components reacted are in a mole ratio of 1 mole polyglycerol, 0.5 to 1 mol dimer acid, and 0.2 to 1.7 mole fatty acid.

In another embodiment, the components reacted are in a mole ratio of 1 mole polyglycerol, 0.5 to 0.75 mol dimer acid, and 0.4 to 1.35 mole isostearic acid.

In another embodiment, the components reacted are in a mole ratio of 1 mole polyglycerol, 0.5 to 0.7 mol dimer acid, and 0.65 to 1 mole isostearic acid.

In another embodiment, the components reacted are in a mole ratio of 1 mole polyglycerol, 0.5 to 1 mol hydrogenated dimer acid, and 0.2 to 1.7 mole isostearic acid.

In another embodiment, the components reacted are in a mole ratio of 1 mole polyglycerol, 0.5 to 0.75 mol hydrogenated dimer acid, and 0.4 to 1.35 mole isostearic acid.

In another embodiment, the components reacted are in a mole ratio of 1 mole polyglycerol, 0.5 to 0.7 mol hydrogenated dimer acid, and 0.65 to 1 mole isostearic acid.

In another embodiment, the components reacted are in a mole ratio of 1 mole polyglycerol-3, 0.5 to 1 mol hydrogenated dimer acid, and 0.2 to 1.7 mole isostearic acid.

In another embodiment, the components reacted are in a mole ratio of 1 mole polyglycerol-3, 0.5 to 0.75 mol hydrogenated dimer acid, and 0.4 to 1.35 mole isostearic acid.

In another embodiment, the components reacted are in a mole ratio of 1 mole polyglycerol-3, 0.5 to 0.7 mol hydrogenated dimer acid, and 0.65 to 1 mole isostearic acid.

In one most preferred embodiment, the components reacted are in a mole ratio of 1 mole polyglycerol-3, 0.5 mole hydrogenated C36 dimer acid, and 1 mole isostearic acid.

In another most preferred embodiment, the components reacted are in a mole ratio of 1 mole polyglycerol-3, 0.67 mole hydrogenated C36 dimer acid, and 0.67 mole isostearic acid.

By adjusting the fatty acid end-cap mole ratio and balancing the amount of polyglycerol and dimer acid, it is possible to control the degree of dimer acid-polyglycerol-extension and end-capping so that cross-linking, for example, via trimer acid, leads to much higher viscosities.

The target viscosity of the pure polymer should be >50,000 cP and less than 5,000,000 cP at 25° C.

In one preferred embodiment, the target viscosity is >75,000 cP and <2,500,000 at 25° C.

In another preferred embodiment, the target viscosity is >100,000 cP and <2,000,000 at 25° C.

In a most preferred embodiment, the target viscosity is >1,000,000 cP and <2,000,000 at 25° C., which leads to further water resistance improvements.

The disclosed polymers are characterized by weight-average molecular weights >2500 Da and <1,000,000 Da measured with GPC using linear polystyrene standards. The GPC column used for these tests consisted of: Phenolgel, 300×4.6 mm; a continuous phase of Tetrahydrofuran (THF) was used and injected at 0.35 mL/min, with the column oven held at 40° C.; a 50 μL injection, and Wyatt refractive index Ri detector. The calibration standards used were strictly linear polystyrene made to be mono-dispersed. Narrow-range polystyrene GPC calibration standards were prepared in mobile phase and had peak molecular weights of 1,290,000 Da; 560,000 Da; 65,500 Da; 28,500 Da; 10,100 Da; 1,680 Da; 580 Da and 208 Da. From standard methodologies, the weight-average and number-average molecular weight are automatically calculated by standard GPC software. We focus here on weight-average molecular weight determinations, which we abbreviate herein as "$M_w$." While $M_w$ can be quite informative in most cases, it is known that the radius of gyration of fully dissolved cross-linked polymers is smaller than for dissolved ideal linear polymers of the same molecular weight and monomer composition. This reduction in size for similar actual molecular weights is characterized as a "polymer contraction factor"; see the literature such as Zimm-Stockmayer Contraction Factor and others. The magnitude of the contraction factor will depend on monomer selection, trimer percentage, and percent conversion, and the substantially non-sequential reaction conditions described above. In our analytical tests, we compare low molecular weight fractions (less than 1000 Da) to both GPC data and measurements of residual monomer of the materials used in the polymerization example, for instance, polyglycerol-3, hydrogenated dimer acid, and isostearic acid. In this way, for the polyester polymers of this disclosure, a contraction factor of around 3 was been determined. This is an important consideration. However, to be consistent with standard GPC methodology, the molecular weight determinations are reported as the "as measured" $M_w$ determinations, relative to linear polystyrene are reported without correction for the contraction factor. Instead, we report the novel combination of $M_w$ (vs linear polystyrene standards) in combination with the viscosity of the same polymer, where a higher viscosity can be directly measured and increases significantly for branched polymers, which would in turn have high contraction factors, such as 3 or more.

In a preferred embodiment, the disclosed polymers have a weight-average molecular weight >4000 Da and <250,000 Da measured with GPC using linear polystyrene standards.

In a most preferred embodiment, the disclosed polymers have a weight-average molecular weight >5000 Da and <150,000 Da measured with GPC using linear polystyrene standards.

As noted above, U.S. Pat. No. 6,242,499 proposes esterifying polyglycerol with fatty acid in a first step and, after most, or all, of the fatty acid has reacted, in a second step adding polyfunctional carboxylic acid and continuing the esterification reaction. This in turn could lead to limited development of molecular weight and lower viscosity polymers which would not provide good waterproofing behavior.

We have found that superior waterproofing properties are provided by certain combinations of $M_w$ and viscosities afforded by the 1-step processing described herein. The polyester polymers of this disclosure were measured using an MCR302 Rheometer from Anton Paar Inc. Roughened or smooth 50 mm diameter twin flat plates were used, covered with polymer sample, adjusted to a gap of 0.5 to 1 mm, and both temperature and shear rate sweeps performed. The polymers of this disclosure display Newtonian behavior and thus have a constant viscosity over a wide range of shear rates. Also, the polymers of this disclosure demonstrated a reduced viscosity with temperature. Thus, measures of viscosity are reported at a precisely controlled temperature and typically as a shear-rate of $1\ s^{-1}$. The values are reported in unit of centipoise (cP). 1000 cP is equivalent to 1 Pascal-second (Pa-s). As noted above, the combination of measured viscosity in combination with the $M_w$ of the polymers measured by GPC using linear polystyrene standards is one important parameter to defining the waterproofing polymers of this disclosure.

In one embodiment, the waterproofing polymer exhibits a combination of $M_w$>2500 Da and <1,000,000 Da measured with GPC using linear polystyrene standards and viscosity of neat polymer >50,000 cP and <5,000,000 cP at 25° C.

In another embodiment, the waterproofing polymer exhibits a combination of $M_w$>4000 Da and <250,000 Da measured with GPC using linear polystyrene standards and viscosity of neat polymer >75,000 cP and <2,500,000 cP at 25° C.

In yet another embodiment, the waterproofing polymer exhibits a combination of $M_w$>5000 Da and <150,000 Da measured with GPC using linear polystyrene standards and viscosity of neat polymer >100,000 cP and <2,000,000 cP at 25° C. In a preferred embodiment, the waterproofing polymer is a substantially or completely non-sequential reaction product of the following components: (i) at least one polyglycerol comprising at least 25% by weight diglycerol, at least 45% by weight triglycerol, and at least 10% by weight tetraglycerol, in each case based on a total weight of polyglycerol; (ii) at least one hydrogenated dimer acid containing at least 60% by weight of hydrogenated C36 diacid and 5-25% by weight of hydrogenated C54 triacid, in each case based on a total weight of hydrogenated acid; and (iii) isostearic acid; wherein the waterproofing polymer exhibits a combination of Mw>5000 Da and <150,000 Da measured with GPC using linear polystyrene standards and viscosity of neat polymer >100,000 cP and <2,000,000 cP at 25° C.

As described extensively above, the reaction sequence and non-sequential reaction, the ratio of polyglycerol to dimer acid and to monoacid are very important for the creation of preferred combinations of viscosity and molecular weight. By definition, these ratios of polyol to mono and polyacid, when driven to completion, will define the so-called degree of esterification. In polycondenstation reactions, such as are the basis of the polyester polymer of this disclosure, one typically includes an excess of either the polyol moieties or the polyacid moities. Mono acids cannot by definition lead to polymerization, but rather only act as end-caps. Due to the presence of 5 hydroxyl groups in polyglycerol-3, the polyol monomer and its hydroxyl moieties in this invention disclosure serves as the ideal and only candidate to be held in excess. If one were to try to react all hydroxyl groups with the large fatty acid groups invention disclosed, the reaction could both lead to intractably high MW and gelation, rendering the product hard to handle and less suitable for use as a cosmetic ingredient. From the preferred mole ratios, we can thus calculate that we prefer a total degree of esterification of available polyglycerol hydroxyl moieties (total esterification) of from 24% to 74% and a degree of esterification of available polyglycerol hydroxyl moieties by dimer acid alone (esterification with dimer acid) of 20% to 40%. Most importantly, the degree of esterification by the end-cap units (esterification with monoacid) are also set in this disclosure and it is important to maintain the esterification with monoacid from 4% to 40%.

We more prefer a total esterification of 28% to 57% with an esterification with dimer acid of 20% to 30% and an esterification with monoacid between 8% and 27%.

We still more prefer a total esterification of 33% to 48% with an esterification with dimer acid of 20% to 28% and an esterification with monoacid between 13% and 20%.

We still more prefer a total esterification of 24% to 74% with an esterification with hydrogenated dimer acid of 20% to 40% and an esterification with monoacid between 4% and 40%.

We still more prefer a total esterification of 28% to 57% with an esterification with hydrogenated dimer acid of 20% to 30% and an esterification with monoacid between 8% and 27%.

We most prefer a total esterification of around 40% with an esterification with hydrogenated dimer acid of around 20% and an esterification with monoacid of around 20%.

We also most prefer a total esterification of around 40% with an esterification with hydrogenated dimer acid of around 27% and an esterification with monoacid of around 13%.

In a preferred embodiment, the waterproofing polymer is a substantially or completely non-sequential reaction product of the following components: (i) at least one polyglycerol comprising at least 25% by weight diglycerol, at least 45% by weight triglycerol, and at least 10% by weight tetraglycerol, in each case based on a total weight of polyglycerol; (ii) at least one hydrogenated dimer acid containing at least 60% by weight of hydrogenated C36 diacid and 5-25% by weight of hydrogenated C54 triacid, in each case based on a total weight of hydrogenated acid; and (iii) isostearic acid; wherein the waterproofing polymer exhibits a combination of Mw>5000 Da and <150,000 Da measured with GPC using linear polystyrene standards and viscosity of neat polymer >100,000 cP and <2,000,000 cP at 25° C.; and wherein the waterproofing polymer is also characterized by a total esterification of about 40%, an esterification with hydrogenated dimer acid of about 27%, and an esterification with monoacid of about 13%.

In practice, since the raw ingredients contain a range of polyglycerol units and a range of dimer and trimer acid content, the above numbers can be adjusted using the actual (and non-theoretical) hydroxyl moities and carboxylic acid moieties as they are determined by standard methods such as mass spectrometry, NMR, and liquid chromatography. The above esterification ranges are based on the idealized structure of polyglycerol-3 and C36-dimer acid. Actual ranges may thus be slightly different than the values given above and can be calculated based on these analytical analyses.

It is most practical to define the extent of polymerization by the final acid value. The initial acid values, in light of the distribution of polyglycerol, monoacid, and polyacid moieties present, can be reliably calculated using the actual acid value determined by the raw ingredient used.

For one example, the initial total Acid Value ("AV" which is commonly defined as mg KOH/g total reactant) is 135 AV. This includes 68 AV for dimer acid and 67 AV for isostearic acid of one preferred embodiment containing 1 mole polyglycerol-3, 0.5 mole hydrogenated C36 dimer acid, and 1 mole isostearic acid. All preferred ratio embodiments described above have corresponding initial AV that can be calculated. When during course of the polymerization reaction, the AV units are reduced, this ratio gives the percent conversion of the reaction from total initial reactive acid moieties to final residual acid moieties. Thus, the completion of reaction is the 1 minus the ratio of final AV to initial AV.

In one embodiment, the polymers of this disclosure have final acid values of 0.1 to <25 mg KOH/g polymer.

In a preferred embodiment, the polymers have final acid values 0.1 to <10 mg KOH/g polymer.

In a most preferred embodiment, the polymers have final acid values 0.1 to <5 mg KOH/g polymer.

Expressing completion of reaction as 1−Final/Initial AV, the completion of reaction of such reactor mixtures to final polymer is >80%.

In a preferred embodiment, the completion of reaction of such reactor mixtures to final polymer is >90%.

In a most preferred embodiment, the completion of reaction of such reactor mixtures to final polymer is >95%.

Particularly for facilitating transportation of the polymer, the polymer can be combined with an organic solvent.

In one embodiment, the solvent is selected from the group consisting of preferably volatile solvents that can be easily removed, such as but not limited to methanol, ethanol, isopropanol, glycerol, propanediol, and the like.

If necessary, the polymer can also optionally be diluted with a variety of emollients to lower the viscosity of the blend at room temperature. Emollients can include any appropriate oil, solvent, ester, triglyceride, ether, silicone, hydrocarbon, etc. that is appropriate for the end use application. For suncare emulsions and products, typical emollients include Triheptanoin, Isopropyl Palmitate, Isopropyl myristate, Triheptanoin (and) C13-C16 Isoparaffin, Heptyl Undecylenate, Caprylic/Capric Triglyceride, Diisooctyl Succinate, C13-C16 Isoparaffin (and) Heptyl Undecylenate, C12-C15 alkyl benzoate, Caprylic/Capric Triglyceride, and other appropriate esters. Emollients can also include ethers, such as dicaprylyl ether. When diluted with emollient, the addition is done with the end-product held with mixing at around 80° C.-100° C. The combination is then further cooled to 50-70° C. for discharging from the reactor and placement into storage.

In one embodiment, the polymer is diluted to a final concentration of from 10 wt % to 99 wt % polymer, where the diluent is a suitable emollient for skin and personal care applications, consisting of an ester or triglyceride.

In another embodiment, the polymer is diluted to a final concentration of from 30 wt % to 90 wt % polymer, where the diluent is a suitable emollient for skin and personal care applications, consisting of an ester or triglyceride from the list given above.

In yet another embodiment, the polymer is diluted to a final concentration of from 50 wt % to 80 wt % polymer, where the diluent is a suitable emollient for skin and personal care applications, consisting of an ester or triglyceride. In one embodiment, at least a portion of the acid groups have been neutralized with a cosmetically acceptable neutralizing agent. Suitable neutralizing agents are all those described in U.S. Patent Publication No. 2018/0318193, the relevant contents of which are hereby incorporated herein by reference.

The film forming polymer can be partially neutralized or fully neutralized by the neutralizing agent. In certain example embodiments between about 5% and about 100% the acid groups on the film forming polymer will be neutralized. In other example embodiments up to about 90%, up to about 80%, up to about 70%, up to about 60%, up to about 50%, up to about 40%, up to about 30%, up to about 25%, up to about 20%, up to about 15%, up to about 10% or up to about 5% of the acid groups on the film forming polymer will be neutralized.

Sunscreen compositions according to the invention are prepared as non-aqueous, volatile solvent-based compositions. The terms "non-aqueous" and "anhydrous" are used interchangeably herein and refer to compositions containing less than about 10% by weight water. Thus, the compositions comprise a single liquid phase that may further comprise dispersed particulates. In certain embodiments the compositions of the invention will contain less than about 5% by weight water or less than 1% by weight water. Example volatile solvents include one or more of alcohols such as methanol, ethanol and isopropanol, volatile hydrocarbons such as isooctane, isododecane, and isohexadecane, aldehydes and volatile silicones also including volatile ketones such as acetone and methyl ethyl ketone. In an embodiment of this invention the volatile solvent is chosen from the group consisting of ethanol, methanol, isopropanol and acetone. The sunscreen compositions of the invention containing alcohol based solvent systems are characterized as non-aqueous solutions. However, it may be desirable to have small amount of water in the composition, for example as a processing aid or co-solvent. In certain example embodiments, the water contents of the compositions will be no greater than about 9% water so as to prevent the active to phase separate or precipitate out of solution. Those of ordinary skill in the art will recognize that different actives have different tolerance for water in solution and will adjust water content accordingly. Additionally, the solvent can include an oil such as mineral or vegetable oil. The oil may be the only solvent or may be used in varying amounts as a co-solvent or as described herein as "emollients".

Emollients can include any appropriate oil, solvent, ester, triglyceride, etc. that is appropriate for the end use application. For suncare products, typical emollients include Triheptanoin, Isopropyl Palmitate, Triheptanoin (and) C13-C16 Isoparaffin, Heptyl Undecylenate, Caprylic/Capric Triglyceride, Diisooctyl Succinate, C13-C16 Isoparaffin (and) Heptyl Undecylenate, C12-C15 alkyl benzoate, Caprylic/Capric Triglyceride, and other appropriate esters. When diluted with emollient, the addition is done with the end-product held with mixing at around 80° C.-100° C. The combination is then further cooled to 50-70° C. for storage.

In one embodiment, the polymer is diluted to a final concentration of from 10 wt % to 99 wt % polymer, where the diluent is a suitable emollient for skin and personal care applications, consisting of an ester or triglyceride.

In another embodiment, the polymer is diluted to a final concentration of from 30 wt % to 90 wt % polymer, where the diluent is a suitable emollient for skin and personal care applications, consisting of an ester or triglyceride from the list given above.

In yet another embodiment, the polymer is diluted to a final concentration of from 50 wt % to 80 wt % polymer, where the diluent is a suitable emollient for skin and personal care applications, consisting of an ester or triglyceride.

The polymer can be incorporated into anhydrous formulations to impart waterproofing properties thereto.

In one embodiment, the waterproofing polymer is incorporated into anhydrous formulations in an amount of 0.1 to 10 wt % based on a total weight of the formulation.

In another embodiment, the waterproofing polymer is incorporated into anhydrous formulations in an amount of 0.5 to 5 wt % based on a total weight of the formulation.

In yet another embodiment, the waterproofing polymer is incorporated into anhydrous formulations in an amount of 1 to 3 wt % based on a total weight of the formulation.

At these amounts, where the anhydrous formulation is a sunscreen formulation, and the waterproofing polymer is prepared from a hydrogenated dimer acid, we have surprisingly discovered the sunscreen formulations are characterized by enhanced SPF. The SPF enhancement has been confirmed in both static SPF and especially in water-resistant SPF (WR SPF) testing.

Sunscreen formulations will typically comprise at least one sunscreen active agent. For purposes of the present disclosure, a "sunscreen active agent" is a material, used singly or in combination with other such materials, that is regarded as acceptable for use as an active sunscreening ingredient based on its ability to absorb UV radiation. Such compounds are generally described by their ability to act as UV active agents and their performance in different spectra regions describes as UV-A, UV-B, or UV-A/UV-B. Approval by a regulatory agency is generally required for inclusion of active agents in formulations intended for human use. Those active agents which have been or are currently approved for sunscreen use in the United States include organic and inorganic substances including, without limitation, para aminobenzoic acid, avobenzone, cinoxate, dioxybenzone, homosalate, menthyl anthranilate, octyl salicylate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum. Examples of additional sunscreen actives that have not yet been approved in the U.S. but are allowed in formulations sold outside of the U.S. include ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. However, as the list of approved sunscreens is currently expanding, those of ordinary skill will recognize that the invention is not limited to sunscreen active agents currently approved for human use but is readily applicable to those that may be allowed in the future.

In Europe, sunscreen active agents approved and, therefore, useful according to the present disclosure, include, again without limitation, benzophenones, for example, Benzophenone-3 (BP3) and Benzophenone-4 (BP4); Salicylates, for example, Homosalate (HMS) and 2-ethylhexyl salicylate (EHS); p-Aminobenzoic acid and derivatives, for example, Ethylhexyl dimethyl PABA (OD-PABA) and 4-p-aminobenzoic acid (PABA); Benzimidazole derivatives, for example, Phenylbenzimidazole sulfonic acid (PMDSA) and Disodium phenyl dibenzimidazole tetrasulfonate (bisdisulizole disodium); Triazines, for example, Ethylhexyltriazone (OT), Diethylhexyl butamido triazone (DBT), and Bis-ethylhexyloxyphenol methoxyphenyl triazine (EMT); Benzotriazoles, for example, Drometrizole trisiloxane (DRT) and Methylene bis-benzotriazolyl tetramethylbutylphenol (MBP, biscotrizole); Dibenzoylmethane derivatives, for example, 4-tert-Butyl-4'-methoxydibenzoylmethane (BM-DBM, avobenzone); Cinnamates, for example, Ethylhexyl methoxycinnamate (OMC) and Isoamyl p-methoxycinnamate (IMC, amiloxate); and Camphor derivatives, for example, Terephtalydene dicamphor sulfonic acid (PDSA), 3-benzylidene camphor (3BC), Benzylidene camphor sulfonic acid (BCSA), 4-methylbenzylidene camphor (4-MBC), Polyacrylamidomethyl benzylidene camphor (PBC), and Camphor benzalkonium methosulfate (CBM).

In one embodiment of the disclosure, the sunscreen active agent comprises a photoprotecting effective amount of particulates of at least one inorganic pigment or nanopigment, non-limiting examples of which include titanium dioxide, zinc oxide, iron oxide, zirconium oxide, cerium oxide, or mixture thereof.

Generally, the sunscreen active agent is present in the sunscreen formulation in amounts well-known in the art to be effective to protect a user to be exposed or already exposed to sunlight from the damaging effects of exposure to sunlight. Typically, these amounts range from 1-25% by weight, preferably 3-25% by weight based on a total weight of the sunscreen formulation.

The disclosed sunscreen formulations may contain a wide range of additional, optional components which are referred to herein as "cosmetic components", but which can also include components generally known as pharmaceutically active agents. The CTFA Cosmetic Ingredient Handbook, Seventh Edition, 1997 and the Eighth Edition, 2000, which is incorporated by reference herein in its entirety, describes a wide variety of cosmetic and pharmaceutical ingredients commonly used in skin care compositions, which are suitable for use in the compositions of the present invention. Examples of these functional classes disclosed in this reference include: absorbents, abrasives, anticaking agents, antifoaming agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, SPF boosters, waterproofing agents, and viscosity increasing agents (aqueous and nonaqueous).

The sunscreen formulations disclosed are applied to the skin as a liquid rub on but can also be applied as a spray. However, the anhydrous formulations disclosed can take other forms, for example, as a lipstick, make-up, lip-balm, eye-shadow, hair dyes and conditioners, or any application where sun protection may be deemed beneficial.

The disclosure will now be described in greater detail with reference to the following non-limiting examples.

EXAMPLES

Compound Examples

A. General Procedures

As described in the copending application, we prefer to use a reaction in which all monomers are added in a single addition, with or without any acid or base catalysts, the reaction vessel placed under vacuum or under nitrogen sparge, or under a combination of vacuum and nitrogen sparge. The reaction mixture is heated with stirring in either a constant ramp or a step-wise ramp to a temperature of 160° C. to 250° C. over a time of 10 min to 10 hours, where it is held at a temperature of 160° C. to 250° C. for 2 to 10 hours.

We more prefer to ramp to 200° C., either linearly or step-wise, over 20 min to 8 hours, where it is held at a temperature of 180° C. to 210° C. for 2 to 6 hours.

We most prefer to ramp to 200° C., either linearly or step-wise, over 2 hours to 5 hours, where it is held at a temperature of 195° C. to 205° C. for 3 to 5 hours.

For example, a useful waterproofing polymer was prepared as follows: A mixture of 24.0 gm polyglycerol-3, 28.2 gm dimer acid and 28.4 gm isostearic acid (CAS #30399-84-9), and 0.24 gm sodium hydroxide was added to a reaction vessel with a downward distillation setup. The mixture was stirred and heated to 180° C. and held at 180° C. for 30 minutes. Then the mixture temperature was increased to 190° C. for 30 minutes and continued to 200° C. The mixture was held at 200° C.-205° C. for about 2-4 hours until reaching a final acid value less than 3.0 meq KOH/ml by titration method. Condensation moisture was removed during the reaction process via the distillation setup. The end-product was cooled to about 100° C.-120° C. before decanting at 100% active.

B. Water-Resistant Polymers

Following the general procedures outlined above, the polymers in the following table were produced.

| Example | PG-3 Type | Ratio of PG-3:DA:ISA | Hydrogenated | Catalyst |
|---------|-----------|----------------------|--------------|----------|
| 4 | A | 1:0.5:1 | No | $H_3PO_3$ |
| 5 | A | 1:0.67:0.67 | No | $H_3PO_3$ |
| 6 | A | 1:0.5:1 | Yes | $H_3PO_3$ |
| 7 | A | 1:0.67:0.67 | Yes | $H_3PO_3$ |
| 8 | B | 1:0.5:1 | Yes | $H_3PO_3$ |
| 9 | B | 1:0.67:0.67 | Yes | $H_3PO_3$ |
| 10 | B | 1:0.5:1 | Yes | NaOH |

In the foregoing table, PG-3 "Type A" is a homemade polyglycerol composed of 17.62 wt % glycerol, 25.4 wt % diglycerol, 18.46 wt % triglycerol, 12.15 wt % tetraglycerol, 8.09 wt % pentaglycerol, 5.48 wt % hexaglycerol, 3.69 wt % heptaglycerol, 2.43 wt % octaglycerol, 1.46 wt % nonaglycerol, 0.83 wt % decaglycerol, 0.37 wt % undecaglycerol, and 0.16 wt % dodecaglycerol.

PG-3 "Type B", available from Inovyn, has a narrower oligoglycerol distribution, and is composed of 30.6 wt % diglycerol, 49.41 wt % triglycerol, 14.78 wt % tetraglycerol, 3.86 wt % pentaglycerol, 1.10 wt % hexaglycerol, 0.28 wt % heptaglycerol, and 0.07 wt % octaglycerol.

C. Comparison to Industry Standards (SPF WR)

The water-resistant SPF of the prepared polymers was compared to a control and certain industry standards shown in the following table.

| Example | Polymer |
|---------|---------|
| 1 | No polymer control |
| 2 | Ganex™ V216 |
| 3 | Ganex™ V220 |
| 11 | Schercemol™ PDD |
| 12 | Isolan™ PDI |

Ganex™ V216 is vinyl pyrollidone and hexadecene copolymer (INCI: VP/HEXADECENE), which is available from Ashland Corporation. It is a synthetic polymer, performs for waterproofing in sunscreen formulations, but is non-performing in biodegradability, and is liquid at 25° C.

Ganex™ V220 is a blend of polyvinyl pyrollidone (PVP) and a copolymer of vinyl pyrollidone and eicosane (INCI: PVP (AND) VP/EICOSENE), which is available from Ashland Corporation. It is a synthetic polymer, performs for waterproofing in sunscreen formulations, but is non-performing in biodegradability, and is solid at 25° C.

Schercemol™ PDD is a different non-performing polymer consisting of PG-3, DA, and ISA, which is available from Lubrizol.

Isolan™ PDI is a different non-performing polymer consisting of PG-3, DA, and ISA, which is available from Evonik Corporation.

As is standard in the art, UV absorption through plastic films coated with UV-absorbing suncare formulation used to mimic human skin is measured with a spectrophotometer to provide a measure of sun protection factor (SPF). SPF is simply the ratio of the initial light to the transmitted light through the UV absorbing film. If 100% is reduced to 10%, the SPF is 10. If 100% is reduced to 1%, the SPF is 100. SPF 50 corresponds to 2% of the UV light being transmitted through the skin.

In each case, a UV-absorbing film having a surface area of 100 cm$^2$ is coated with 20×5 mg drops of an anhydrous composition containing the test polymer and subjected to UV light in the 290 to 400 nm range to provide a so-called "static" SPF measurement.

SPF Water Resistance (SPF WR) measurements are taken from the same film after placing it in a water-bath, heated to 40° C., and subjecting to mild agitation. The sample after withdrawing is gently dried and again measured for light transmission, this time providing SPF WR data.

Data are provided in the copending application showing the polymers of the present disclosure provide SPF WR in oil-in-water sunscreen formulations at least as good and in many cases superior to some industry standards. Further, when the waterproofing polymer is prepared from hydrogenated dimer the SPF WR is superior even to the industry gold standards.

Among the waterproofing polymers of the present disclosure, the effects of hydrogenation and differences in polymer weight-average molecular weight are illustrated in the FIGURE. Clearly, the use of hydrogenated dimer acid can increase SPF WR significantly. Additional gains can be realized by producing the waterproofing polymer to a greater weight-average molecular weight.

D. Exemplary Anhydrous Formulations

An anhydrous formulation was made to exemplify a solid or "stick" sunscreen paste. Such pastes are applied and rubbed into smaller areas of skin such as around the nose and face. For this example, a first oil phase was made in a 1000 mL beaker with an overhead stirrer, in which the following ingredients were added and heated to 80-85 C: 8.3 g Example 13 (consisting of 60% Polymer Example 10 and 40% Caprylic-Capric Triglyceride), 15 g avobenzone (Neo Heliopan 357, Symrise), 75 g homosalate (Neo Heliopan® HMS, Symrise), 25 g ethylhexyl salicylate (Neo Heliopan® OS, Symrise), 50 g octocrylene (Neo Heliopan® 303, Symrise), 15 g dimethicone (DOW CORNING® 200 Fluid, Dow Corning), 35 g Octyldodecyl Neopentanoate (and) Octyldodecyl Alcohol (and) Neopentanoic Acid (Elefac I-205, Alzo Inc.), 35 g Neopentyl Glycol Diethylhexanoate (and) Neopentyl Glycol Diisostearate (Minno 21, Alzo Inc). In a separate 500 mL beaker, the following solid ingredients were mixed then added to the heated liquid ingredients with stirring: 50 g Ozokerite wax (Strahl & Pitsch Inc), 35 g beeswax (White Beeswax Pastilles SP-422P, Strahl & Pitsch Inc), 51.7 g paraffin (Paraffin Wax SP-173, Strahl & Pitsch Inc), and 25 g polyethelene (Performalene 400, New Phase Technologies). After dissolving all, the sample was removed from heat, 12.5 g OSA starch was added until dispersed (DRY-FLO® PC Nouryon) and the resulting mixture was cooled in molds for use as a stick product.

In-Vitro Testing was carried out using formulation example 13, which was designed to have SPF and WR SPF of at least 30. The In-Vitro SPF and WR SPF were measured using the method described employing artificial skin (partially-hydrophilic acrylic polymer material). The In-Vitro SPF results showed SPF of 48 and WR SPF of 42, both above the SPF target of 30 based on UV absorbing and scattering ingredients of this formulation. This example shows that the polymer of this disclosure provides waterproofing benefit in an anhydrous formulation.

The other waterproofing polymers disclosed, as well as other waterproofing polymers made according to the methods described can be made into sticks and other anhydrous formulations that should provide similar benefits.

While the present disclosure has been described in conjunction with the specific embodiments set forth above, many alternatives, modifications and other variations thereof will be apparent to those of ordinary skill in the art. All such alternatives, modifications and variations are intended to fall within the spirit and scope of the present disclosure.

What is claimed is:

1. An anhydrous formulation comprising a waterproofing polymer that is a reaction product of the following components: (i) at least one polyglycerol; (ii) at least one dimer acid; and (iii) at least one fatty acid having 8-30 carbon atoms;

wherein (iii) and (i) are in a molar ratio of less than 2:1; and wherein the at least one polyglycerol comprises a mixture of oligoglycerols having the following oligomer distribution:
   (a) 0 to 30 wt % glycerol;
   (b) 10 to 40 wt % diglycerol;
   (c) 10 to 65 wt % triglycerol;
   (d) 2 to 25 wt % tetraglycerol;
   (e) 0 to 15 wt % pentaglycerol;
   (f) 0 to 15 wt % hexaglycerol;
   (g) 0 to 10 wt % heptaglycerol;
   (h) 0 to 10 wt % octaglycerol;
   (i) 0 to 5 wt % nonaglycerol; and
   (j) 0 to 5 wt % decaglycerol;
   wherein all weight percentages are based on 100 wt % of the at least one polyglycerol.

2. The formulation according to claim 1, wherein the waterproofing polymer is a completely non-sequential reaction product.

3. The formulation according to claim 1, wherein the waterproofing polymer is produced from polyglycerol composed of at least 40% by weight, based on a total weight of the polyglycerol, of a combination of diglycerol and triglycerol.

4. The formulation according to claim 1, wherein the waterproofing polymer is produced from at least one hydrogenated dimer acid.

5. The formulation according to claim 4, wherein the waterproofing polymer is produced from hydrogenated dimer acid obtained through dimerization of unsaturated C18 fatty acids and subsequent hydrogenation.

6. The formulation according to claim 5, which contains a trimer acid content ranging from about 5-25 wt %, based on a total weight of hydrogenated dimer acid.

7. The formulation according to claim 1, wherein the waterproofing polymer is produced from at least one fatty acid selected from the group consisting of: caprylic acid, pelargonic acid, capric acid, undecylic acid, lauric acid, tridecylic acid, myristic acid, pentadecylic acid, palmitic acid, margaric acid, stearic acid, isostearic acid, nonadecylic acid, arachidic acid, behenic acid, and lignoceric acid.

8. The formulation according to claim 7, wherein the waterproofing polymer is produced from isostearic acid.

9. The formulation according to claim 1, wherein the waterproofing polymer is produced from: (i) polyglycerol composed of at least 40% by weight, based on a total weight of the polyglycerol, of a combination of diglycerol and triglycerol; (ii) C18 hydrogenated dimer acid having a trimer acid content ranging from about 5-25 wt %, based on a total weight of hydrogenated dimer acid; and (iii) isostearic acid.

10. The formulation according to claim 1, wherein the waterproofing polymer exhibits a combination of $M_w$>2500 Da and <1,000,000 Da measured with gel permeation chromatography using linear polystyrene standards and viscosity of neat polymer >50,000 cP and <5,000,000 cP at 25° C.

11. An anhydrous sunscreen formulation comprising: (a) at least one sunscreen active agent; and (b) at least one waterproofing polymer of claim 1.

12. The formulation according to claim 11, wherein the waterproofing polymer is a completely non-sequential reaction product.

13. The formulation according to claim 11, wherein the waterproofing polymer is produced from polyglycerol composed of at least 40% by weight, based on a total weight of the polyglycerol, of a combination of diglycerol and triglycerol.

14. The formulation according to claim 11, wherein the waterproofing polymer is produced from at least one hydrogenated dimer acid.

15. The formulation according to claim 14, wherein the waterproofing polymer is produced from hydrogenated dimer acid obtained through dimerization of unsaturated C18 fatty acids and subsequent hydrogenation.

16. The formulation according to claim 15, which contains a trimer acid content ranging from about 5-25 wt %, based on a total weight of hydrogenated dimer acid.

17. The formulation according to claim 11, wherein the waterproofing polymer is produced from at least one fatty acid selected from the group consisting of: caprylic acid, pelargonic acid, capric acid, undecylic acid, lauric acid, tridecylic acid, myristic acid, pentadecylic acid, palmitic acid, margaric acid, stearic acid, isostearic acid, nonadecylic acid, arachidic acid, behenic acid, and lignoceric acid.

18. The formulation according to claim 17, wherein the waterproofing polymer is produced from isostearic acid.

19. The formulation according to claim 11, wherein the waterproofing polymer is produced from: (i) polyglycerol composed of at least 40% by weight, based on a total weight of the polyglycerol, of a combination of diglycerol and triglycerol; (ii) C18 hydrogenated dimer acid having a trimer acid content ranging from about 5-25 wt %, based on a total weight of hydrogenated dimer acid; and (iii) isostearic acid.

20. The formulation according to claim 11, wherein the sunscreen active agent is at least one member selected from the group consisting of: para aminobenzoic acid, avobenzone, cinoxate, dioxybenzone, homosalate, menthyl anthranilate, octyl salicylate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, bis-ethylhexyloxyphenol methoxyphenyltriazine, 4-methylbenzylidenecamphor, homosalate, butyl methoxydibenzoylmethane, octocrylene, octyl salicylate, bemotrizinol and isopentyl 4-methoxycinnamate, benzophenone-3 (BP3), benzophenone-4 (BP4), homosalate (HMS), 2-ethylhexyl salicylate (EHS), ethylhexyl dimethyl PABA (OD-PABA), 4-p-aminobenzoic acid (PABA), phenylbenzimidazole sulfonic acid (PMDSA), disodium phenyl dibenzimidazole tetrasulfonate (bisdisulizole disodium), ethylhexyltriazone (OT), diethylhexyl butamido triazone (DBT), bis-ethylhexyloxyphenol methoxyphenyl triazine (EMT), drometrizole trisiloxane (DRT), methylene bis-benzotriazolyl tetramethylbutylphenol (MBP, biscotrizole), 4-tert-butyl-4'-methoxydibenzoylmethane (BM-DBM, avobenzone), ethylhexyl methoxycinnamate (OMC), isoamyl p-methoxycinnamate (IMC, amiloxate), terephtalydene dicamphor sulfonic acid (PDSA), 3-benzylidene camphor (3BC), benzylidene camphor sulfonic acid (BCSA), 4-methylbenzylidene camphor (4-MBC), polyacrylamidomethyl benzylidene camphor (PBC), camphor benzalkonium methosulfate (CBM), titanium dioxide, zinc oxide, iron oxide, zirconium oxide, cerium oxide, and mixtures thereof.

21. The formulation according to claim 11, wherein the waterproofing polymer exhibits a combination of $M_w$>2500 Da and <1,000,000 Da measured with gel permeation chromatography using linear polystyrene standards and viscosity of neat polymer >50,000 cP and <5,000,000 cP at 25° C.

22. A method of protecting a user to be exposed or already exposed to sunlight from the damaging effects of exposure to sunlight, said method comprising applying to skin of said user an effective amount therefor of a sunscreen formulation according to claim 11.

23. A method of making an anhydrous sunscreen formulation, said method comprising the steps of:
providing (a) at least one sunscreen active agent;
providing (b) at least one waterproofing polymer; and
combining (a) and (b) to form the anhydrous sunscreen formulation,
wherein the at least one waterproofing polymer is a substantially non-sequential reaction product of the following components: (i) at least one polyglycerol; (ii) at least one dimer acid; and (iii) at least one fatty acid having 8-30 carbon atoms;
wherein (iii) and (i) are in a molar ratio of less than 2:1; and
wherein the at least one polyglycerol comprises a mixture of oligoglycerols having the following oligomer distribution:
(a) 0 to 30 wt % glycerol;
(b) 10 to 40 wt % diglycerol;
(c) 10 to 65 wt % triglycerol;
(d) 2 to 25 wt % tetraglycerol;
(e) 0 to 15 wt % pentaglycerol;
(f) 0 to 15 wt % hexaglycerol;
(g) 0 to 10 wt % heptaglycerol;
(h) 0 to 10 wt % octaglycerol;
(i) 0 to 5 wt % nonaglycerol; and
(j) 0 to 5 wt % decaglycerol; and
wherein all weight percentages are based on 100 wt % of the at least one polyglycerol.

24. The method according to claim 23, wherein the waterproofing polymer is a completely non-sequential reaction product.

25. The method according to claim 23, wherein the waterproofing polymer is produced from polyglycerol composed of at least 40% by weight, based on a total weight of the polyglycerol, of a combination of diglycerol and triglycerol.

26. The method according to claim 23, wherein the waterproofing polymer is produced from at least one hydrogenated dimer acid.

27. The method according to claim 26, wherein the waterproofing polymer is produced from hydrogenated dimer acid obtained through dimerization of unsaturated C18 fatty acids and subsequent hydrogenation.

28. The method according to claim 27, which contains a trimer acid content ranging from about 5-25 wt %, based on a total weight of hydrogenated dimer acid.

29. The method according to claim 24, wherein the waterproofing polymer is produced from at least one fatty acid selected from the group consisting of: caprylic acid, pelargonic acid, capric acid, undecylic acid, lauric acid, tridecylic acid, myristic acid, pentadecylic acid, palmitic acid, margaric acid, stearic acid, isostearic acid, nonadecylic acid, arachidic acid, behenic acid, and lignoceric acid.

30. The method according to claim 29, wherein the waterproofing polymer is produced from isostearic acid.

31. The method according to claim 23, wherein the waterproofing polymer is produced from: (i) polyglycerol composed of at least 40% by weight, based on a total weight of the polyglycerol, of a combination of diglycerol and triglycerol; (ii) C18 hydrogenated dimer acid having a trimer acid content ranging from about 5-25 wt %, based on a total weight of hydrogenated dimer acid; and (iii) isostearic acid.

32. The method according to claim 23, wherein the waterproofing polymer exhibits a combination of $M_w$ >2500 Da and <1,000,000 Da measured with gel permeation chromatography using linear polystyrene standards and viscosity of neat polymer >50,000 cP and <5,000,000 cP at 25° C.

33. An anhydrous formulation comprising a waterproofing polymer that is a reaction product of:
(i) a polyglycerol comprising a combination of diglycerol, triglycerol, tetraglycerol, pentaglycerol, hexaglycerol, heptaglycerol, and octaglycerol; and optionally one or more of glycerol, nonaglycerol, decaglycerol, undecaglycerol, dodecaglycerol, and combinations thereof;
(ii) a C36 hydrogenated dimer acid; and
(iii) isostearic acid;
wherein (i), (ii) and (iii) are reacted in a molar ratio of about [1:(0.5 to 0.67): (0.67 to 1)].

34. The anhydrous formulation of claim 33 wherein the polyglycerol is free of the glycerol, nonaglycerol, decaglycerol, undecaglycerol, and the dodecaglycerol.

35. The anhydrous formulation of claim 33 wherein the polyglycerol comprises a combination of the glycerol, nonaglycerol, decaglycerol, undecaglycerol, and the dodecaglycerol.

36. A sunscreen formulation comprising:
(a) a sunscreen active agent comprising a combination of avobenzone, ethylhexyl salicylate, homosalate, and octocrylene; and
(b) the anhydrous formulation of claim 33.

37. The sunscreen formulation of claim 36 wherein the waterproofing polymer is the reaction product of:
(i) the polyglycerol comprising the combination of diglycerol, triglycerol, tetraglycerol, pentaglycerol, hexaglycerol, heptaglycerol, and octaglycerol;
(ii) the C36 hydrogenated dimer acid; and
(iii) the isostearic acid;
wherein (i), (ii) and (iii) are reacted in a molar ratio of about 1:0.5:1.

38. The sunscreen formulation of claim 37 further comprising caprylic-capric triglyceride.

* * * * *